(12) United States Patent
Batten et al.

(10) Patent No.: US 7,997,156 B1
(45) Date of Patent: Aug. 16, 2011

(54) F.O.G. SAMPLE PORT

(75) Inventors: William C. Batten, Asheboro, NC (US);
Bruce W. Kyles, Asheboro, NC (US);
Randolph H. Batten, Asheboro, NC (US)

(73) Assignee: Thermaco, Inc., Asheboro, NC (US)

( * ) Notice: Subject to any disclaimer, the term of this patent is extended or adjusted under 35 U.S.C. 154(b) by 731 days.

(21) Appl. No.: 12/120,692

(22) Filed: May 15, 2008

Related U.S. Application Data (60) Provisional application No. 60/938,083, filed on May 15, 2007.

(51) Int. Cl.
*G01N 1/00* (2006.01)

(52) U.S. Cl. .................................. 73/863.86; 73/864.51

(58) Field of Classification Search .................... None
See application file for complete search history.

(56) References Cited

U.S. PATENT DOCUMENTS

| | | | | |
|---|---|---|---|---|
| 4,744,256 A * | 5/1988 | Niskin | | 73/864.66 |
| 4,986,138 A * | 1/1991 | Spencer | | 73/864.34 |
| 5,005,432 A * | 4/1991 | Faulkner | | 73/863.86 |
| 5,172,332 A * | 12/1992 | Hungerford et al. | | 700/267 |
| 5,413,005 A | 5/1995 | Gray | | 73/863.43 |
| 5,974,900 A * | 11/1999 | Kalidindi | | 73/863.57 |
| 6,423,548 B1 * | 7/2002 | Newberg et al. | | 436/174 |
| 6,976,398 B2 * | 12/2005 | Leoncavallo et al. | | 73/863.52 |

OTHER PUBLICATIONS

5. Fog Sampling, pp. 18-25 from Considerations for Management of the Discharge of FOG to Sanitary Sewer Systems, undated related technology.
Typical Grease Interceptor & Sample Port Installation from the City of Lubock Water Utilities; undated related technology.
Typical Grease Interceptor Installation; Des Moines Metro Wastewater Reclamation Authority, undated related technology.
Sample Port Detail, Palo Alto Sewer Use Ordinance 16.09.060; Oct. 2000.

* cited by examiner

*Primary Examiner* — Robert R Raevis
(74) *Attorney, Agent, or Firm* — MacCord Mason PLLC (57) ABSTRACT

A F.O.G. water sampling apparatus includes a housing having an inlet, an outlet, a floor that slopes downward from the inlet to the outlet and an open top. A first insert placed in the housing for normal operation includes a pipe having end flanges making a friction fit within the housing and connecting the inlet and outlet and spanning above the housing floor. A second, substitute insert to receive a F.O.G. sampling jar has a floor that slopes downward from the inlet to the outlet and at the floor of the housing.

20 Claims, 6 Drawing Sheets

F.O.G. SAMPLE PORT

This application is entitled to the benefit of the filing date of provisional application Ser. No. 60/938,083, filed on May 15, 2007.

BACKGROUND OF THE INVENTION

Fat, oil, and grease contaminant removal or recovery systems are well known in the prior art. Over the past thirty years there has been a steady move towards requiring food handling facilities to have systems for servicing kitchen grease-bearing water flows. Sewer system lines can become clogged from the fats, oil and grease waste materials (hereinafter referred to as "F.O.G.") put into the sewer system from food handling facilities. This has led more and more sewer authorities to implement F.O.G. control programs. These programs regulate food handling facilities and the manner in which they process F.O.G. The object of many of these programs is to ensure that food handling facilities remove as much of the oil and grease as possible from the effluent flow, thereby releasing only grey water to the sewer system.

As part of the compliance programs, sewer authorities want to check up on the efficacy of the F.O.G. removal program. Some localities are mandating that F.O.G. sampling ports be installed downstream of the F.O.G. removal facility, so that the authorities can check to see the quality of the effluent to determine whether it falls within the requirements. Various Gerry-rigged installations have been known in the prior art, but they have various drawbacks that lead to undesirability.

SUMMARY OF THE INVENTION

The present invention fulfills one or more of these needs in the art by providing an apparatus for enabling water samples to be taken to assess F.O.G. levels. A housing has an inlet, an outlet, a floor that slopes downward from the inlet to the outlet, and an open top. A first insert for placement in the housing for normal operation includes a pipe having a length to snugly fit within the housing and connect the inlet and outlet when placed within the housing. A second insert for placement in the housing facilitates receipt of a sample jar for F.O.G. sampling, connects the inlet and outlet when placed in the housing, and has a floor that slopes downward from the inlet to the outlet and at the floor of the housing to enable placement of a sampling jar on the sloping floor of the second insert to receive effluent from the inlet.

An embodiment of the apparatus for enabling water samples to be taken to assess F.O.G. levels includes a housing having an inlet and an outlet, the housing having a floor that slopes downward from the inlet to the outlet and an open top. A first insert for placement in the housing for normal operation, includes a pipe having flanges at each end, the pipe and flanges having a length to make a friction fit within the housing with the pipe connecting the inlet and outlet when placed with the friction fit in the housing and spanning spaced above the floor of the housing. A second insert for placement in the housing facilitates receipt of a sample jar for F.O.G. sampling and includes flanges at each end. The second insert and its flanges have a length to make a friction fit within the housing and connect the inlet and outlet when placed with the friction fit in the housing. The second insert has a floor that slopes downward from the inlet to the outlet and at the floor of the housing.

Preferably, end walls of the housing having the inlet and outlet are not parallel to one another and the flanges of the first insert are not parallel to one another, so that both flanges of the first insert are not in friction fit contact with the end walls of the housing until pressed into place. Likewise, the flanges of the second insert are not parallel to one another, so that both flanges of the second insert are not in friction fit contact with the end walls of the housing until pressed into place.

Advantageously, the inlet and outlet of the housing are generally in line with one another without a significant change in height.

In a preferred embodiment, the housing and the inserts are made of plastic.

The housing may have an open top to enable the inserts to be inserted downward through the open top. The sloping floor of the housing has an upper end at an inlet end of the housing and the upper end of the floor is spaced below the bottom of the inlet so that effluent entering the housing through the inlet can fall as a waterfall to a sample jar placed in the second insert during F.O.G. sampling.

Preferably, the floor of the second insert has a cylindrical configuration with a cylindrical axis parallel to the slope of the floor to position a cylindrical sampling jar. More preferably, the floor of the second insert has a reduced diameter near the inlet to receive a shoulder of a sampling jar.

The housing floor may have an upwardly-extending flange near the inlet and the second insert may have a downwardly extending flange at its inlet end to enable the flange on the second insert to hook onto the flange on the housing floor.

The invention can also be considered as a F.O.G. sampling port including a housing made and configured for installation below ground. The housing has an inlet connectable to a branch of a Tee pipe placed for a carrying effluent that may include F.O.G. The inlet leads into the housing and connects through a valve in the housing to an outlet downstream of the valve. The housing has an access path above the valve and the outlet so that a sampling jar can be lowered through the access path to collect effluent that may include F.O.G. from the outlet. A ground key can be inserted through the access path to open the valve to release effluent that may include F.O.G. from the outlet into the sampling jar.

Preferably, the outlet in the housing discharges downwardly. Desirably, the housing also has a lid for the housing to cover the access path.

An extension collar may be included to mount to a top of the housing to extend the access path a variable distance to compensate for variable depths of placement of the housing below ground.

In preferred embodiments a cradle on an outside of the housing engages and connects with an outside of the Tee pipe carrying effluent that may include F.O.G. More preferably, the inlet leading into the housing has a diameter and the configuration of the cradle to connect with a Tee pipe is such that the connection is to a reducing Tee pipe having a diameter at least three times greater than the diameter of the inlet leading into the housing.

BRIEF DESCRIPTION OF THE DRAWINGS

The invention will be better understood by a reading of the Detailed Description of the Examples of the Invention along with a review of the drawings, in which.

DETAILED DESCRIPTION OF EXAMPLES OF THE INVENTION

The apparatus provides a housing that is to be connected to piping that is downstream of an apparatus that removes fats, oils, and grease (F.O.G.). The housing has pipe fittings, so that it can be connected to upstream and downstream pipe portions to make a continuous path for the effluent. The housing has a chamber with a floor sloping downhill from the intake to the discharge side. A first insert includes a pipe segment having upstream and downstream flanges that is put into place for standard operations when sampling is not taking place. When sampling is to take place the first insert is removed and second insert is placed within the housing and provides for positioning of a sampling jar. In the sampling position, the sampling jar is placed below the upstream pipe portion of the housing, so that a waterfall effect from the influent takes place, causing some turbulence of the flow and good mixing of the sample in the sample jar.

When sampling is complete, the second insert is removed and replaced with the pipe segment. Both of the sampling insert and pipe segment can be removed by lifting them out an open top on the housing. They are reinstalled by reversing that movement.

Figure 1:
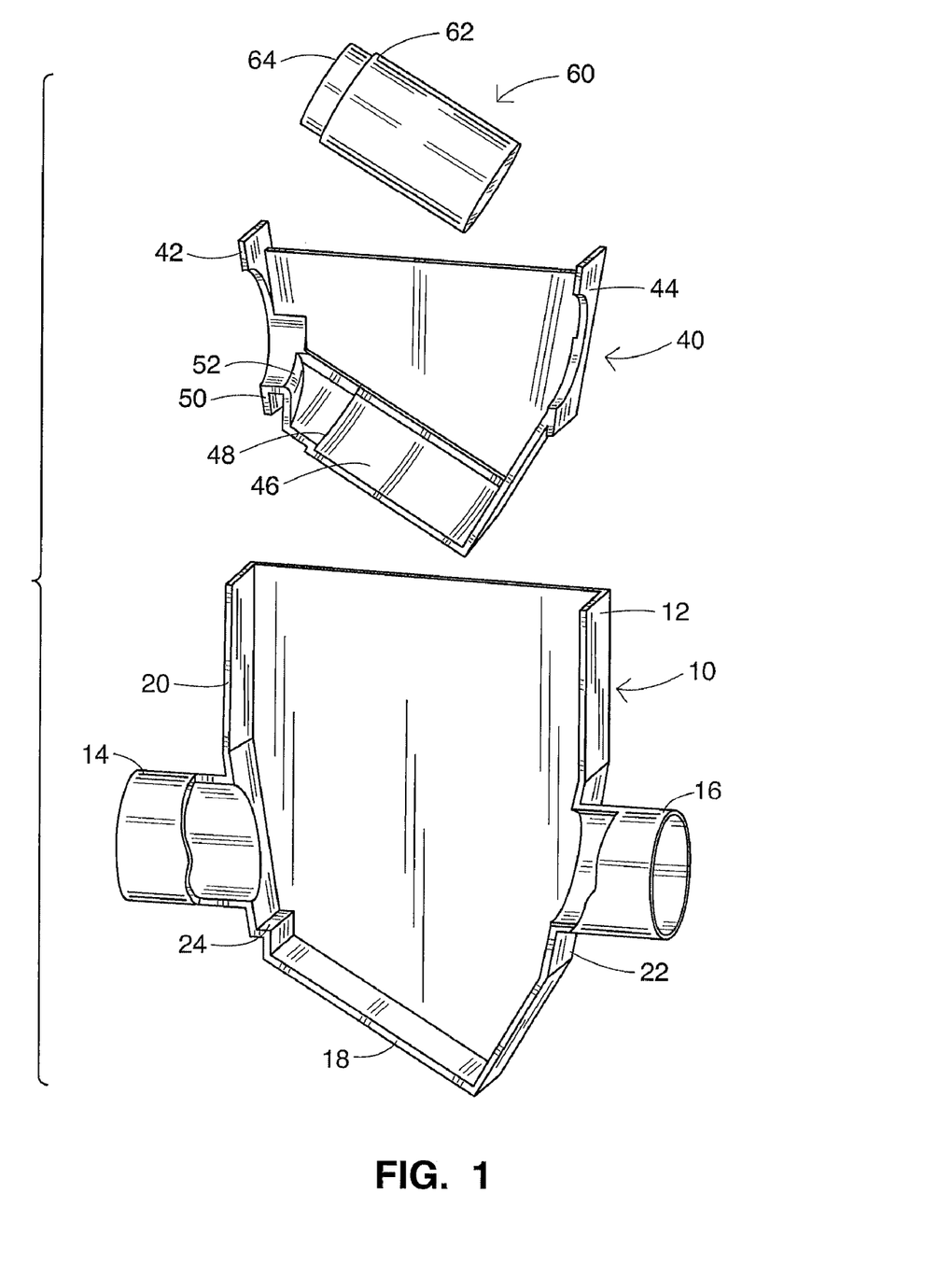
FIG. 1 is an exploded view of an embodiment of the invention depicting the second insert.

As seen in FIG. 1, a housing is provided to be connected inline and downstream of the F.O.G. removal apparatus. The housing 10 has an upstanding head space 12, an inlet 14 and an outlet 16. The inlet 14 is to be connected downstream of the F.O.G. removal device to receive effluent from the F.O.G. removal device. The F.O.G. removal device can be any of several types including BIG DIPPER and TRAPZILLA products of Thermaco, Inc., Asheboro, N.C., or other point source removal devices or grease traps. The outlet 16 discharges effluent to the sewer system. The installation can be such that the headspace chamber 12 has an open top that can be covered with a suitable removable cover. The apparatus can be installed in a manhole, for example, with a manhole cover.

The housing 10 has a downwardly sloping floor 18, sloping from the inlet 14 to the outlet 16. At its upstream or inlet end 14 the floor 18 has a flange 24 to be discussed later. Below the headspace 12, the housing 10 has end walls 20 and 22 surrounding the inlet 14 and outlet, 16, respectively. As can be seen, the two end walls 20 and 22 are not parallel, but rather are slightly further apart at their tops than at their bottoms.

Figure 2:
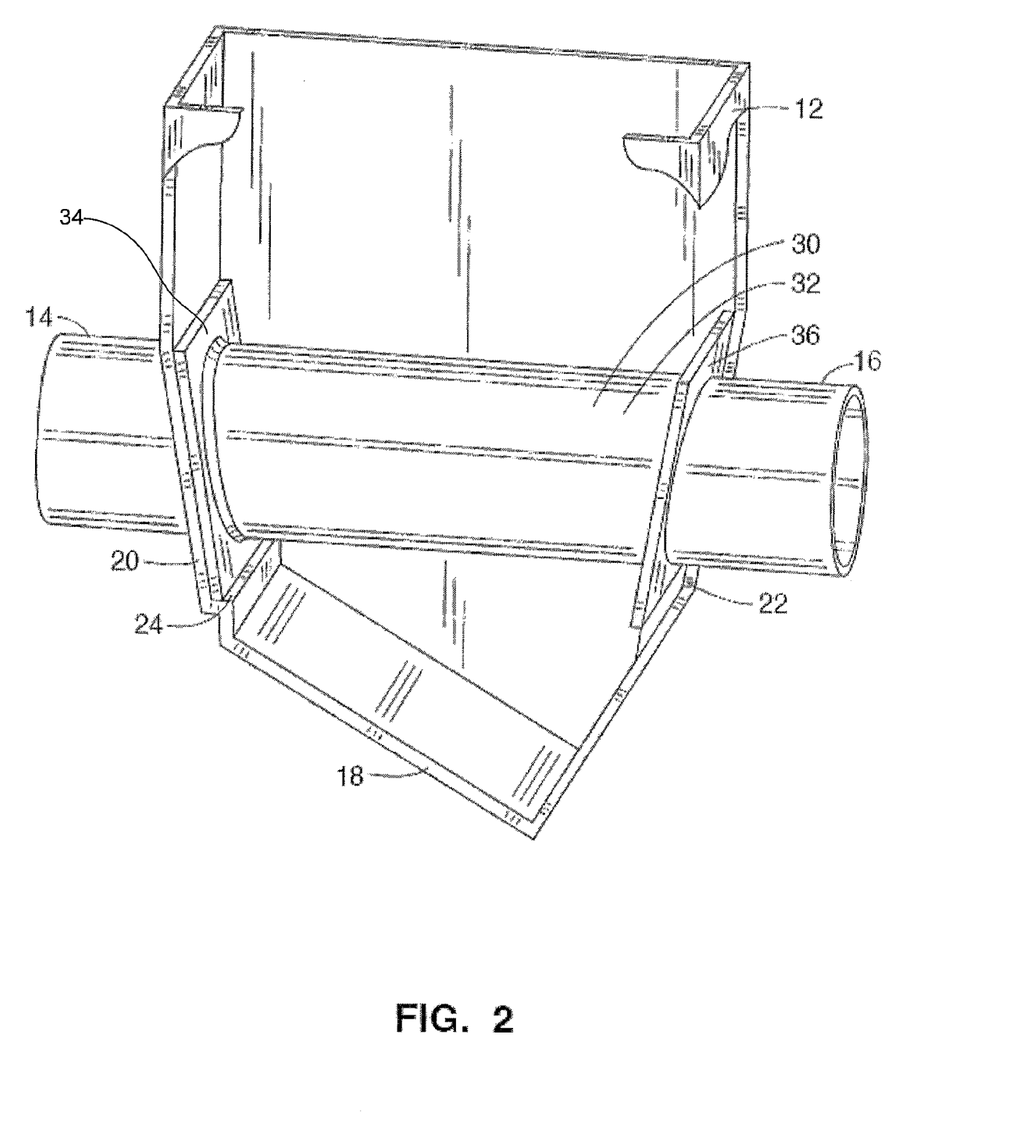
FIG. 2 is a sectional view of the embodiment of FIG. 1 with the first insert in place.

The non-parallel nature of the end walls 20 and 22 is better seen in FIG. 2. FIG. 2 shows a first insert 30 in place. The insert 30 is primarily made up of a conduit or pipe 32 having end flanges 34 and 36. The flanges 34 and 36 are likewise not parallel, but have an angle that matches the angle between the end walls 20 and 22. The insert 30 can be inserted through the open top of the headspace 12 and pressed downwardly, so that the flanges 34 and 36 form a friction between the end walls 20 and 22. In this condition, the apparatus acts as a conduit, so that the effluent can pass from the inlet 14 through the conduit 32 and out of the outlet 16, substantially uninterrupted. This is the condition of the housing for most of its operation.

Figure 3:
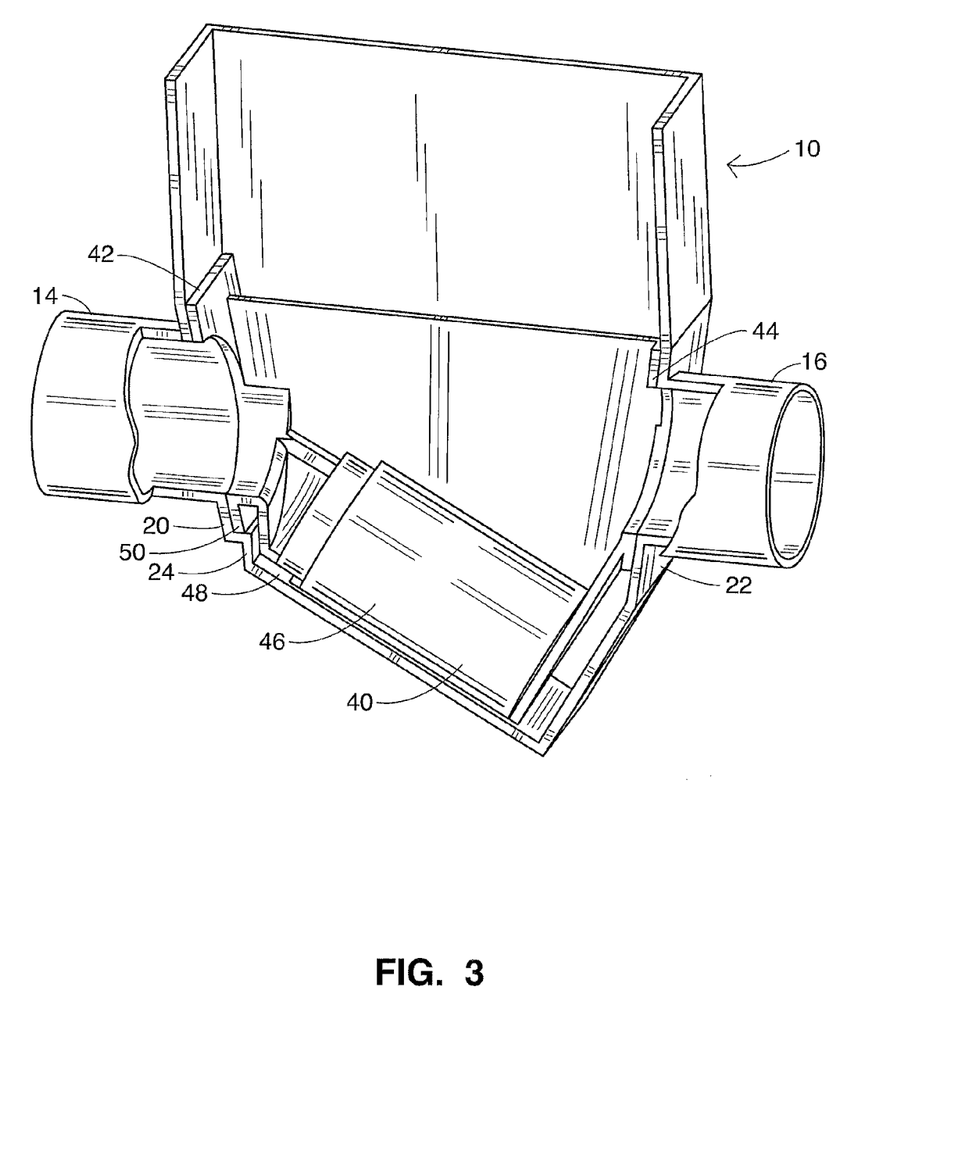
FIG. 3 is a perspective view of the embodiment of FIG. 1 with the second insert in place, partially broken away.

When it is desired to use the sampling port to take a sample, the insert 30 is removed by pulling upward through the headspace and replaced with a second insert 40, seen in FIGS. 1 and 3. The second insert 40 also has non-parallel end walls 42 and 44 substantially matching the end walls 34 and 36 of the first insert and making a similar engagement with the end walls 20 and 22 of the housing 10. The second insert 40 has a sloping floor 46 that is substantially cylindrical in shape, so that it can receive a standard sampling jar 60. A reduced diameter ledge 48 on the floor 46 allows the shoulder 62 of a sampling jar 60 to nest underneath it with an open top 64 of the sampling jar 60 positioned to receive effluent from the inlet 14 spilling over the ledge 52. (See FIG. 1) This ledge 52 provides turbulence or mixing, which some localities require. The floor 46 of the insert also has a downwardly extending flange 50 to engage with the flange 24 on the housing 10.

Thus, when it is desired to take a water sample, the housing 10 is accessed and the first insert 30 is removed from the open top of the housing 10. The second insert 40 is put into place, firmly positioned by the friction fit of the end walls 42 and 44 with the end walls of the housing and the engagement of the flange 50 of the second insert with the flange 24 of the housing. The sampling jar 60 can then be put into place with its shoulder 62 underneath ledge 48 on the floor 46 of the insert 40 and the sample collected. Once the sample is collected, the sampling jar 60 can be removed, capped and taken for analysis. The second insert 40 can also then be removed to be replaced with the first insert 30, so that normal operation can resume.

As can be appreciated, the inlet and outlet are at substantially the same elevation (with only the normal gradient), which makes installation easier. No significant drop in the elevation is required in order to take the desired sample. Also, since any effluent spilled during sampling is collected in the second insert, the housing 10 remains substantially dry, assuming that the first insert is placed quickly after the removal of the second insert.

The housing and the first and second inserts can conveniently be made of plastic, with molded polyethylene currently preferred.

If desired, the device can be provided with one or more extension collars on top of body 10 to increase headspace 12, as needed to reach a suitable height.

Figure 4:
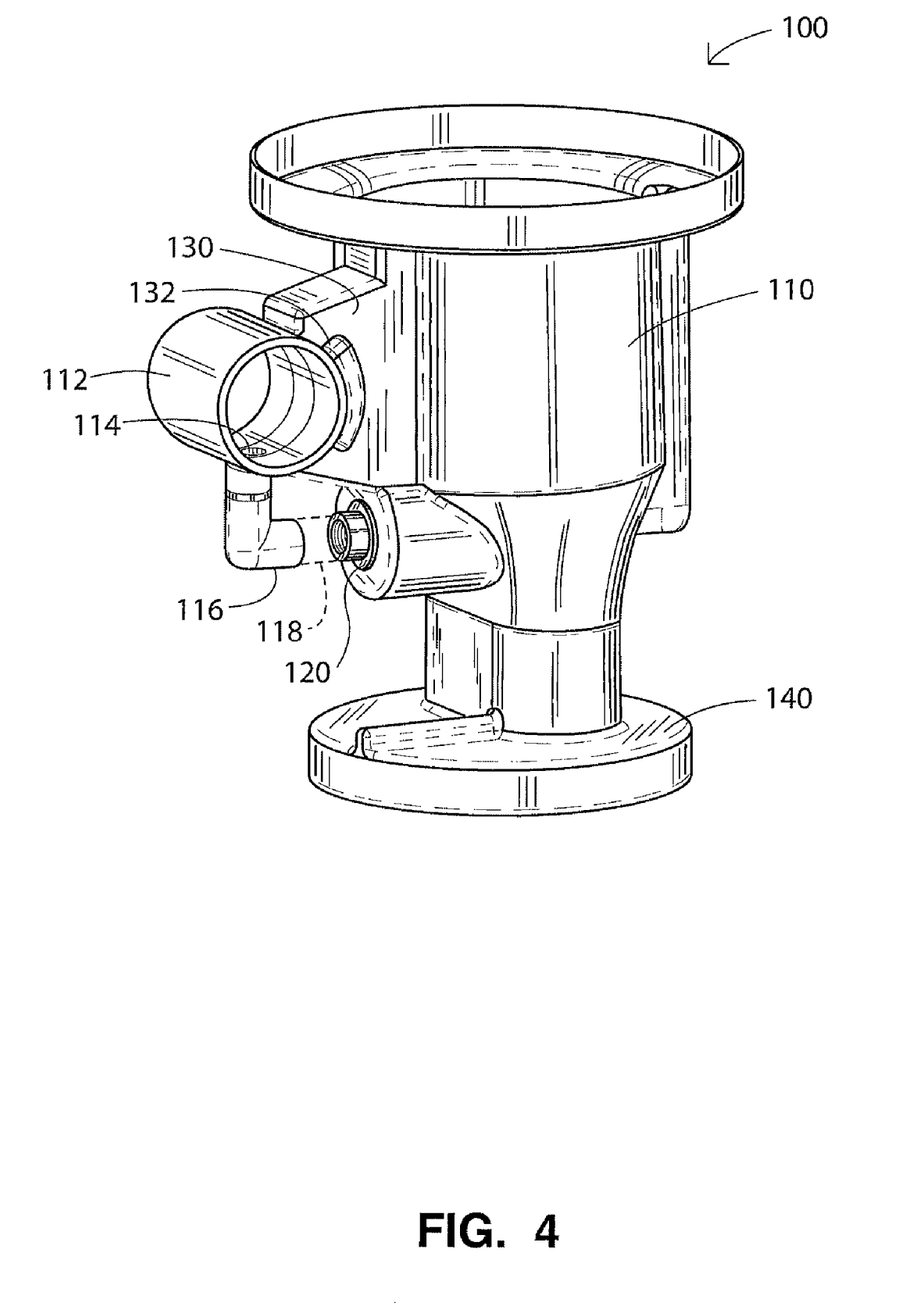
FIG. 4 is a perspective view of an embodiment of the invention.

As seen in FIG. 4, the sample well assembly 100 includes housing 110 that connects to a drain line (not shown) from a grease trap or other effluent generating system. A reducing tee 112 is installed in the drain line, using readily available plumbing fittings. The reducing tee 112 contains a center port 114 that is directed downward into elbow 116. Elbow 116 is connected to horizontal piping 118 and connects to housing 110 through fitting 120. The reducing tee 112 of the main flow path is approximately 4 inches or larger in diameter. The center port 114 is approximately 1 inch diameter. A cradle 130 is molded into the side of housing 110. Cradle 130 interfaces with reducing tee 112. The cradle 130 has projections 132 which will allow reducing tee 112 and housing 110 to be connected together for additional support of the sample well assembly 100. An anchor ring 140 is provided at the base of housing 110. The anchor ring 140 may be affixed to a floor by concrete to secure into a below grade installation.

Figure 5:
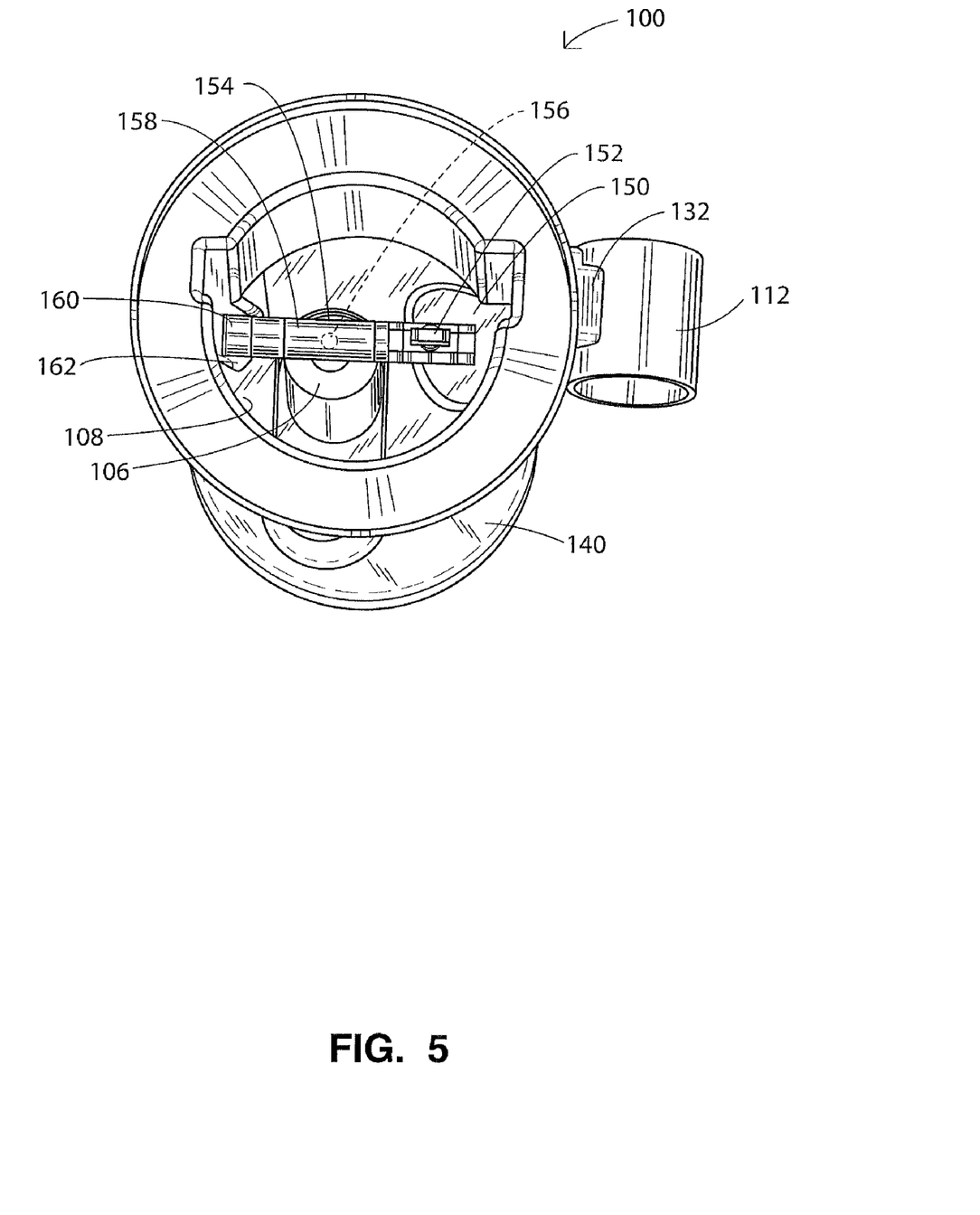
FIG. 5 is a top perspective view showing the inside and parts therein of the embodiment of FIG. 4 with the sampling jar in place.

As seen in FIG. 5, the effluent sample flows from the fitting 120 through ball valve 150. Ball valve 150 connects to handle 152 that is compatible with a "ground key" or "street key" used by the public works department for turning on and off water supply at a water meter. The effluent flow then drains to an approximately 1 inch drain tee 154 positioned with its center port 156 pointing downward. Tee piping 158 continues horizontally to cap 160 that is supported by slot 162 on the back wall 108 of the housing 110. When an effluent sample is being taken, a sample jar 106 is placed under the downward pointing leg 157 (see FIG. 6) of the drain tee 154.

Figure 6:
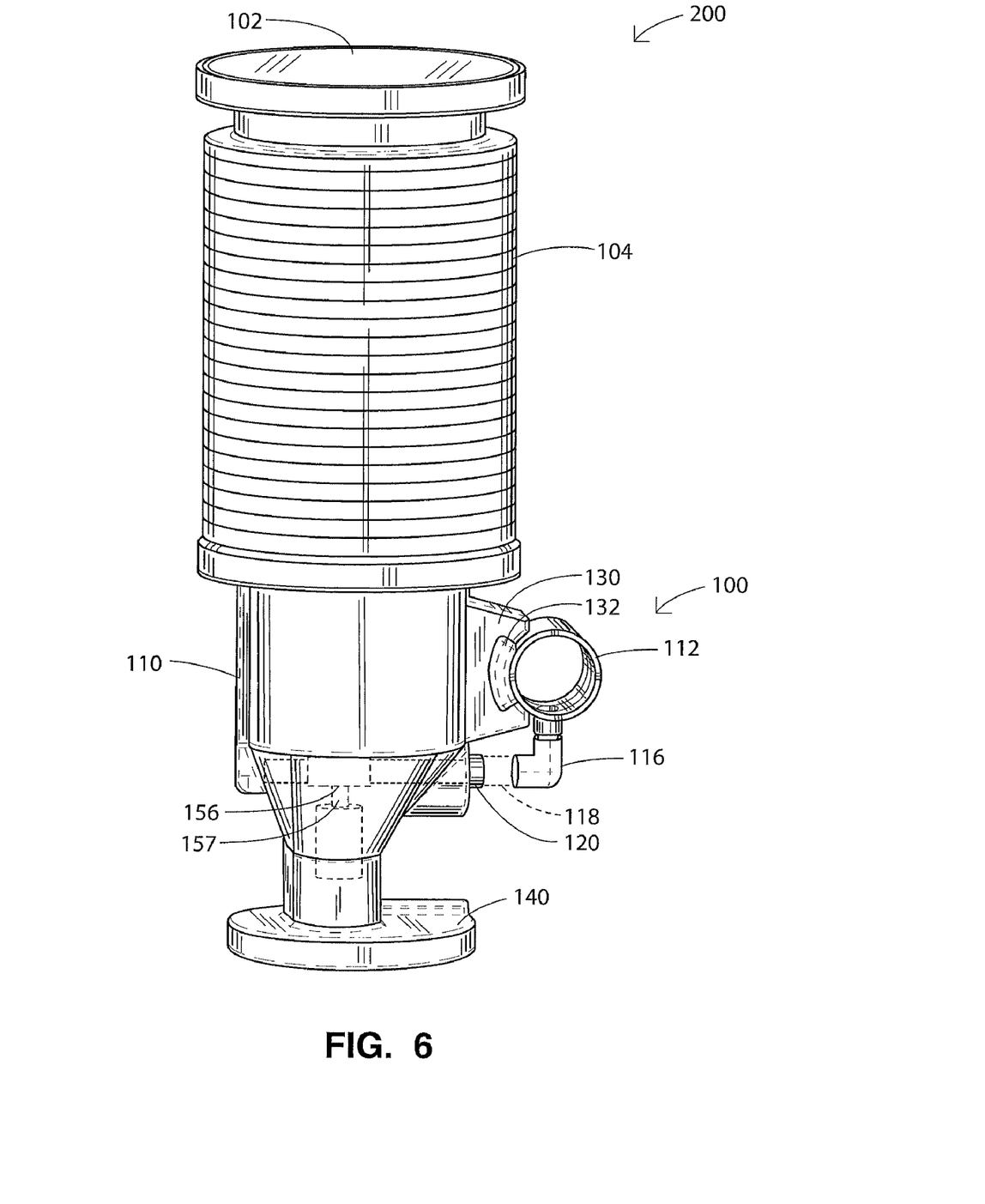
FIG. 6 is a side perspective view of the embodiment of FIG. 4 showing the completed assembly.

FIG. 6 shows a completed unit of an embodiment of the invention. Housing 110 is intended to be placed below grade. Since the distance below grade will vary with every installation, an adjustable extension collar 104 is provided with the sample well assembly 100. The adjustable extension collar 104 can be cut to varying heights to adapt to various conditions. Multiple collars may be installed if necessary. A removable top cover 102 is attached to provide access for sampling.

When is it desired to take an effluent sample from the sample well assembly 100, the housing 110 is accessed through top cover 102. A sample jar 106 is lowered into the housing 110 using a telescoping handle (not shown). Sample jar 106 is positioned under the drain tee 154. Ball valve 150 is opened by way of a "ground key" or a "street key" on the handle 152. The handle 152 is turned on the ball valve 150 to allow effluent to flow into the drain tee piping 154, down the drain tee center port 156, through the downward pointing leg 157 into the sample jar 106. When the desired amount of effluent is collected, the ball valve 150 is then closed by way of the "ground key" or "street key" of the handle 152. The sample jar 106 is then removed from housing 110, by way of the telescoping handle and top cover 102 is replaced. Users may desire to collect two samples, discarding the first sample as a "flush" of the plumbing lines.

Certain modifications and improvements will occur to those skilled in the art upon reading the foregoing description. It should be understood that all such modifications and improvements have been omitted for the sake of conciseness and readability, but are properly within the scope of the following claims.

What is claimed is:

1. An apparatus for enabling water samples to be taken to assess F.O.G. levels comprising
 a housing having an inlet and an outlet, the housing having a floor that slopes downward from the inlet to the outlet and an open top,
 a first insert for placement in the housing for normal operation, including a pipe having flanges at each end, the pipe and flanges having a length to make a friction fit within the housing with the pipe connecting the inlet and outlet and spanning spaced above the floor of the housing when placed with the friction fit in the housing, and
 a second insert for placement in the housing to facilitate receipt of a sample jar for F.O.G. sampling including flanges at each end, the second insert and its flanges having a length to make a friction fit within the housing and connecting the inlet and outlet when placed with the friction fit in the housing and having a floor that slopes downward from the inlet to the outlet and that is located at the floor of the housing.

2. An apparatus as claimed in claim 1 wherein end walls of the housing having the inlet and outlet are not parallel to one another and the flanges of the first insert are not parallel to one another, so that both flanges of the first insert are not in friction fit contact with the end walls of the housing until pressed into place.

3. An apparatus as claimed in claim 1 wherein end walls of the housing having the inlet and outlet are not parallel to one another and the flanges of the second insert are not parallel to one another, so that both flanges of the second insert are not in friction fit contact with the end walls of the housing until pressed into place.

4. An apparatus as claimed in claim 1 wherein the inlet and outlet of the housing are generally in line with one another without a significant change in height.

5. An apparatus as claimed in claim 1 wherein the housing and the inserts are made of plastic.

6. An apparatus as claimed in claim 1 wherein the housing has an open top to enable the inserts to be inserted downward through the open top.

7. An apparatus as claimed in claim 1 wherein the sloping floor of the housing has an upper end at an inlet end of the housing and the upper end of the floor is spaced below the bottom of the inlet so that effluent entering the housing through the inlet can fall as a waterfall to a sample jar placed in the second insert during F.O.G. sampling.

8. An apparatus as claimed in claim 1 wherein the floor of the second insert has a cylindrical configuration with a cylindrical axis parallel to the slope of the floor to position a cylindrical sampling jar.

9. An apparatus as claimed in claim 8 wherein the floor of the second insert has a reduced diameter ledge near the inlet to receive a shoulder of a sampling jar.

10. An apparatus as claimed in claim 1 wherein the housing floor has an upwardly extending flange near the inlet and the second insert has a downwardly extending flange at its inlet end to enable the flange on the second insert to hook onto the flange on the housing floor.

11. An apparatus for enabling water samples to be taken to assess F.O.G. levels comprising
 a housing having an inlet and an outlet that are generally in line with one another without a significant change in height, the housing having a floor that slopes downward from the inlet to the outlet and an upwardly extending flange near the inlet, an open top, and end walls having the inlet and outlet that are not parallel to one another,
 a first insert for placement in the housing for normal operation, including a pipe having flanges at each end, the pipe and flanges having a length to make a friction fit within the housing with the pipe connecting the inlet and outlet when placed with the friction fit in the housing and spanning spaced above the floor of the housing, the flanges of the first insert not being parallel to one another, so that both flanges of the first insert are not in friction fit contact with the end walls of the housing until pressed into place, and
 a second insert for placement in the housing to facilitate receipt of a sample jar for F.O.G. sampling including flanges at each end, the second insert and its flanges having a length to make a friction fit within the housing and connecting the inlet and outlet when placed with the friction fit in the housing, the second insert having a floor that slopes downward from the inlet to the outlet and at the floor of the housing and that has a cylindrical configuration with a cylindrical axis parallel to the slope of the floor to position a cylindrical sampling jar and that has a raised diameter near the inlet to receive a shoulder of a sampling jar and that has a downwardly extending flange on and underside of the floor's inlet end to enable the flange on the second insert to hook onto the flange on the housing floor,
 the end flanges of the second insert not being parallel to one another, so that both flanges of the second insert are not in friction fit contact with the end walls of the housing until pressed into place,
 wherein the sloping floors of the housing and the second insert each have an upper end at an inlet end and the upper end is spaced below the bottom of the inlet so that effluent entering the housing through the inlet can fall as a waterfall to a sample jar placed in the second insert during F.O.G. sampling.

12. An apparatus for enabling water samples to be taken to assess F.O.G. levels comprising
   a housing having an inlet and an outlet, the housing having a floor that slopes downward from the inlet to the outlet and an open top,
   a first insert for placement in the housing for normal operation, including a pipe having a length to snugly fit within the housing and connect the inlet and outlet when placed within the housing, and
   a second insert for placement in the housing to facilitate receipt of a sample jar for F.O.G. sampling, the second insert connecting the inlet and outlet when placed in the housing and having a floor that slopes downward from the inlet to the outlet and at the floor of the housing to enable placement of a sampling jar on the sloping floor of the second insert to receive effluent from the inlet.

13. A method of taking water samples to assess F.O.G. levels comprising
   opening a housing having an inlet connected to an effluent source and an outlet connected to a pipe leading to a sewage treatment plant,
   pulling a first insert from the housing, including releasing a friction fit of a pipe having flanges at each end within the housing to expose the inlet and outlet, and
   placing a second insert in the housing, including pressing the second insert into the housing to make a friction fit of the second insert within the housing and leaving the inlet and outlet exposed to the inside of the second insert, and
   placing a sampling jar in the second insert with an open mouth of the sampling jar disposed to receive effluent from the effluent source incoming into the second insert and housing through the inlet.

14. A method as claimed in claim 13 wherein placing a sampling jar includes engaging a shoulder of a sampling jar against a reduced diameter ledge of a floor of the second insert.

15. A F.O.G. sampling port comprising
   a housing made and configured for installation below ground,
   the housing having an inlet connectable to a branch of a Tee pipe placed for a carrying effluent that may include F.O.G.,
   the inlet leading into the housing and connected to a valve in the housing and an outlet downstream of the valve,
   wherein the housing has an access path above the valve and the outlet so that a sampling jar can be lowered through the access path to collect effluent that may include F.O.G. from the outlet and a ground key can be inserted through the access path to open the valve to release effluent that may include F.O.G. from the outlet into the sampling jar.

16. A F.O.G. sampling port as claimed in claim 15 wherein the outlet in the housing discharges downwardly.

17. A F.O.G. sampling port as claimed in claim 15 further comprising a lid for the housing to cover the access path.

18. A F.O.G. sampling port as claimed in claim 15 further comprising an extension collar mounted to a top of the housing to extend the access path a variable distance to compensate for variable depths of placement of the housing below ground.

19. A F.O.G. sampling port as claimed in claim 15 further comprising a cradle on an outside of the housing to engage and connect with an outside of the Tee pipe carrying effluent that may include F.O.G.

20. A F.O.G. sampling port as claimed in claim 19 wherein the inlet leading into the housing has a diameter and the configuration of the cradle to connect with a Tee pipe is such that the connection is to a reducing Tee pipe having a diameter at least three times greater than the diameter of the inlet leading into the housing.

* * * * *